United States Patent
Fevola et al.

(10) Patent No.: US 7,446,087 B2
(45) Date of Patent: Nov. 4, 2008

(54) COMPOSITIONS COMPRISING LOW-DP POLYMERIZED SURFACTANTS AND METHODS OF USE THEREOF

(75) Inventors: Michael J. Fevola, Belle Meade, NJ (US); Joseph J. LiBrizzi, Hillsborough, NJ (US); Russel M. Walters, Philadelphia, PA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 145 days.

(21) Appl. No.: 11/429,493

(22) Filed: May 5, 2006

(65) Prior Publication Data
US 2007/0259796 A1  Nov. 8, 2007

(51) Int. Cl.
*C11D 3/37* (2006.01)
*C11D 1/88* (2006.01)

(52) U.S. Cl. .................. 510/475; 510/121; 510/123; 510/151; 510/470; 510/474; 510/490; 424/488; 424/70.11; 424/70.13; 424/70.21

(58) Field of Classification Search ............. 510/121, 510/123, 151, 470, 474, 475, 490; 424/488, 424/70.11, 70.13, 70.21
See application file for complete search history.

(56) References Cited

U.S. PATENT DOCUMENTS

| | | | |
|---|---|---|---|
| 4,199,562 A | 4/1980 | Vanlergrghe et al. | |
| 4,362,713 A | 12/1982 | Buck | |
| 4,430,250 A | 2/1984 | Sebag et al. | |
| 4,664,835 A | 5/1987 | Grollier et al. | |
| 4,879,107 A | 11/1989 | Vanlergrghe et al. | |
| 6,210,689 B1* | 4/2001 | Martino et al. | 424/401 |
| 6,358,914 B1 | 3/2002 | Gabriel et al. | |
| 6,627,612 B1* | 9/2003 | O'Lenick et al. | 514/25 |
| 2004/0223925 A1 | 11/2004 | L'Alloret | |
| 2005/0070453 A1* | 3/2005 | Librizzi et al. | 510/130 |

FOREIGN PATENT DOCUMENTS

| | | |
|---|---|---|
| EP | 0308031 B1 | 4/1993 |
| WO | WO 01/23515 A1 | 9/1999 |
| WO | WO 2006/018324 * | 2/2006 |

OTHER PUBLICATIONS

Colonial Chemicals, Inc., Polysuga® Nate—Sulfonated Poly (Alkyl Polyglucosides) Low Irritation Sulfonates, no date given.

* cited by examiner

*Primary Examiner*—Brian P Mruk (57) ABSTRACT

Provided are low-irritation personal care compositions comprising a low-DP polymerized surfactants. Also provided are methods of making and using such compositions.

24 Claims, 1 Drawing Sheet

FIGURE 1

COMPOSITIONS COMPRISING LOW-DP POLYMERIZED SURFACTANTS AND METHODS OF USE THEREOF

FIELD OF INVENTION

The present invention relates to compositions comprising polymerized surfactants and, in particular, compositions comprising polymerized surfactants that are useful in personal care applications and have relatively low irritation associated therewith.

DESCRIPTION OF THE RELATED ART

Synthetic detergents, such as cationic, anionic, amphoteric, and non-ionic surfactants, are used widely in a variety of detergent and cleansing compositions to impart cleansing properties thereto. In addition, in certain compositions (e.g. personal care compositions such as shampoos, washes, etc.), it may be desirable to use combinations and levels of surfactants sufficient to achieve relatively high levels of foam volume and/or foam stability.

However, as is recognized in the art, synthetic detergents tend to be irritating to the skin and eyes. Thus, as levels of such detergents are increased in attempts to increase cleansing and foaming properties associated with certain compositions, the irritation associated with such compositions also tends to increase, making them undesirable for use on or near the skin and/or eyes.

Certain attempts to produce milder cleansing compositions have included combining relatively low amounts of anionic surfactants (which tend to be relatively high-foaming but also relatively highly irritating), with relatively lower irritating surfactants such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Disadvantageously, mild cleansing compositions produced via both of such methods tend to suffer from relatively poor foaming and cleansing performance. Yet another approach described in, Librizzi et al., (in United States Published Patent Application US20050075256 A1) discusses the use of a composition including both a hydrophobically modified polymer and a surfactant to provide low irritation cleansing composition.

Nevertheless, applicants have recognized the need for additional approaches to providing reduced irritation compositions and further recognized the need to provide a variety of compositions and methods having reduced irritation to the skin and/or eye. In addition, in certain embodiments, applicants have recognized the need for compositions that are not only mild to the skin and/or eyes, but additionally exhibit desirable foam properties and/or other desirable aesthetic properties.

SUMMARY OF THE INVENTION

The present invention provides personal care compositions that overcome the disadvantages of the prior art and have relatively low irritation properties associated therewith. In particular, applicants have discovered that certain polymerized surfactants may be used to great advantage to produce compositions having low irritation associated therewith and, in certain embodiments, combinations of additional beneficial aesthetic and other properties.

According to one aspect, the present invention provides a personal care composition comprising a low-DP polymerized surfactant having a PMOD % of less than about 90%.

In another aspect of the invention, provided are compositions comprising a low-DP polymerized surfactant, the compositions having a TEP value of about 3 or greater.

In another aspect of the invention, provided are methods of making personal care compositions comprising combining a polymerized surfactant having a PMOD % of less than about 90% with at least one other personal care component to produce a personal care composition having a CMID % of less than about 90%.

In yet another aspect of the invention, applicants have provided a method of treating the skin, hair, or vaginal region, the method comprising applying to the skin, hair, or vaginal region a composition comprising a low-DP polymerized surfactant having a PMOD % of less than about 90%.

DESCRIPTION OF PREFERRED EMBODIMENTS

All percentages listed in this specification are percentages by weight, unless otherwise specifically mentioned.

As used herein the term "polymerized surfactant" refers to any polymer including repeat units that are amphiphilic, i.e. the repeat units include at least one hydrophilic moiety and at least one hydrophobic moiety.

A "repeat unit" is hereby defined as the smallest combination of chemical species (e.g., ions or atoms) that repeat periodically to generate the polymer. Polymerized surfactants can be visualized as a number of surfactant structures (i.e. amphiphiles) that are linked by a polymer backbone (ref. Anton, P.; Köberle, P.; Laschewsky, A. *Makromol. Chem.*, 1993, 194, 1-27).

As will be readily understood by those of skill in the art, the term "hydrophilic moiety," is any anionic, cationic, zwitterionic, or nonionic group that is polar and generally water-soluble. Nonlimiting examples include anionics such as sulfate, sulfonate, carboxylate, phosphate, phosphonates; cationics such as: ammonium, including mono-, di-, and tri-alkylammonium species, pyridinium, imidazolinium, amidinium, poly(ethyleneiminium); zwitterionics such as ammonioalkylsulfonate, ammonioalkylcarboxylate, amphoacetate; and nonionics such as hydroxyl, sulfonyl, poly(ethyleneoxy).

A "hydrophobic moiety" is hereby defined as any nonpolar, generally water-insoluble group containing seven or more carbon atoms. Certain preferred hydrophobic moieties include moieties comprising about eight or more carbon atoms, more preferably about 10 or more carbon atoms. Certain particular preferred hydrophobic moieties include those having from about 8 to about 12 carbon atoms. Nonlimiting examples of hydrophobic groups include any saturated or unsaturated linear, branched, cyclic, or aromatic hydrocarbon species containing more than five carbon atoms. Functionalities, that may be included in the hydrophobic group are, for example, ether, ester, ketone, amide, carbonate, urethane, carbamate, or xanthate functionalities.

As defined herein, the term, "low-DP polymerized surfactant," refers to a polymerized surfactant, as defined above, which further meets the following criteria (a) and (b): (a) the polymerized surfactant has at least about 7 and less than about 2000 amphiphilic repeat units on a weight average basis; and (b) the amphiphilic repeat units comprise at least about 10 mole % of the polymerized surfactant. Examples of certain preferred low-DP polymerized surfactants included those having 7 to about 2000 amphiphilic repeat units, such as from 10 to about 1000 amphiphilic repeat units, and even more preferably from about 20 to about 500 amphiphilic repeat units. In certain embodiments, the low-DP polymerized surfactants of the present invention preferably comprise least about 25 mole % of amphiphilic repeat units.

As noted above, applicants have discovered unexpectedly that certain polymerized surfactants are suitable for use in producing compositions having relatively low irritation associated therewith. According to certain preferred embodiments, applicants have discovered that low-DP polymerized surfactants having a PMOD % (measured in accord with the procedure described herein below and shown in the Examples) of less than about 90%, more preferably less than about 80%, more preferably less than about 50%, and more preferably less than about 40%, are useful in producing compositions having beneficially low irritation properties associated therewith.

For example, applicants note that the "TEP value" associated with a particular composition, which value is measured conventionally via the Trans-Epithelial Permeability Test ("TEP Test") as set forth in the Invittox Protocol Number 86 (May 1994) incorporated herein by reference and described in further detail in the Examples below, has a direct correlation to the irritation to the skin and/or eyes associated with the composition. More specifically, a higher TEP value of a composition tends to indicate less irritation to the skin and eyes associated therewith as compared to a composition having a lower TEP value, which composition tends to cause higher levels of irritation to the skin and/or eyes. Applicants have recognized that the present compositions have surprisingly high TEP values/lower irritation associated therewith. For example, in certain embodiments, the present compositions have a TEP value of at least about 3 or greater, preferably at least about 3.5 or greater. In certain more preferred embodiments, the compositions produced according to the present methods exhibit a TEP value of at least about 4 or greater, more preferably, at least about 5 or greater, even more preferably, at least about 6 or greater. In certain particularly preferred embodiments, the compositions may, in fact, exhibit such an unexpected and markedly reduced level of irritation, that the TEP score exceeds the measurement capability of the test, and is therefore recorded as "no leakage".

Figure 1:
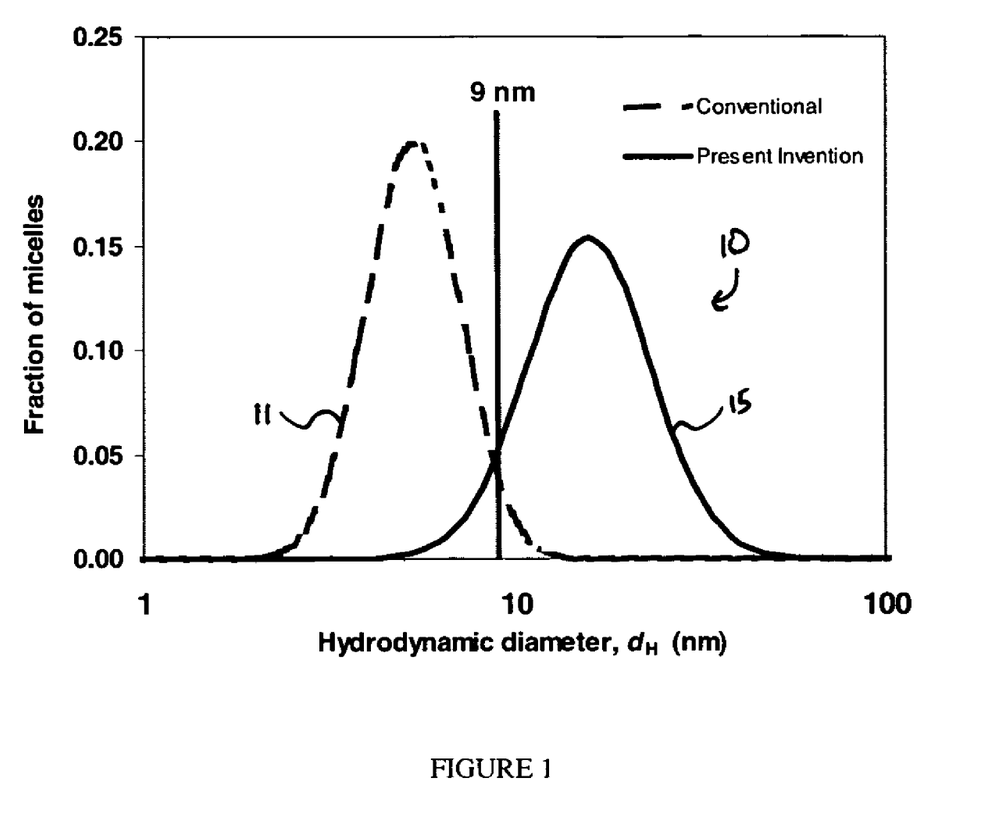
FIG. 1 is a graphical depiction of idealized micelle size distributions for compositions of the present invention and compositions of the prior art.

Applicants have further discovered that two parameters of a composition, the (1) "average micelle hydrodynamic diameter $d_H$," a measure of average micelle size and, in particular (2), the "fraction of micelles with $d_H<9$ nanometers (nm)" provide a measurement of the degree of irritation that may result from compositions that include surfactants. That is, applicants have recognized that surfactant micelles are rarely monodisperse in size and aggregation number (i.e., the average number of molecules of surfactant in a particular micelle). Instead, surfactant micelles tend to exist as a population with distributions of sizes and aggregation numbers that give rise to micelle size distribution functions, as shown by the example in FIG. 1. FIG. 1 is a graph 10 showing a micelle size distribution function for a typical conventional surfactant system, a composition including sodium laureth sulfate and cocamidopropyl betaine (curve 11, generated by fitting an idealized log normal distribution to actual data obtained by testing Comparative Example 19). Applicants have discovered, by comparison, that low-DP polymerized surfactants of the present invention are capable of providing a distribution of micelles that, as shown in curve 15, is "shifted" to favor larger micelles (curve generated by fitting an idealized log normal distribution to actual data obtained by testing Example 12).

Accordingly, applicants have measured the relative small micelle fraction and average micelle size of the compositions of the present invention and comparative compositions as the "CMID %" and "CMIDz", respectively (both measured in accord with the procedures described herein below and shown in the Examples). As detailed below in Tables 7, 11 and 14, applicants have noted that compositions of the present invention tend to exhibit a small micelle fraction, i.e., a fraction of micelles with $d_H<9$ nm, (herein referred to as "CMID %") that is surprisingly low. In one embodiment of the invention, the CMID % of the composition is less than about 90%, more preferably less than about 80%, even more preferably less than about 50%, and most preferably less than about 30%. [Note that for sake of clarity it is emphasized that CMID % relates to the relative irritation associated with a property of a composition (including compositions comprising polymerized surfactants), whereas PMOD % relates to the relative irritation/relative suitability of a polymerized surfactant for use in a composition in accord with preferred embodiments of the invention.]

Applicants have further recognized that the present invention allows for the production of compositions that exhibit not only reduced irritation, but also desirable foam properties. In particular, as detailed in Table 3, applicants have discovered that not only is it possible to formulate compositions that are have low irritation, but said compositions also have substantial foam. For example, in certain embodiments, compositions of the present methods have a foam value of about 25 mL or greater. In certain more preferred embodiments, the compositions produced according to the present methods exhibit a foam value of at least about 50 mL or greater, more preferably, at least about 100 mL.

Applicants have further recognized that the present invention allows for the production of compositions that exhibit not only reduced irritation, but also desirable rheology properties. In particular, applicants have discovered that while certain ingredients such as hydrophobically modified polymers tend to increase the viscosity and the yield point associated with a composition as more polymer is added, the polymerized surfactants of the present invention tend to have relatively small effect on the rheology of the compositions to which they are added. Accordingly, in certain embodiments, higher amounts of the present polymers may be added to more significantly reduce irritation without producing a composition that is too viscous for effective personal use.

In addition, applicants have further discovered unexpectedly that while certain conventional surfactants become substantially more irritating as the concentration of surfactant in a composition is increased beyond a certain point, the polymerized surfactants of the present invention tend not to exhibit the same detrimental increasing irritancy at high concentrations. As shown in Table 14, it can be seen that as concentration of the polymerized surfactant increases from 4.8% to 10%, the CMID % value increases only a small amount, and TEP value is fairly stable as well, indicating that the properties of these compositions are surprisingly "dose independent."

Any of a variety of polymerized surfactants that meet the above criteria may be suitable for the present invention. Although applicants do not wish to be bound by or to any particular theory of operation, it is believed that the polymerized surfactants meeting the above criteria act to reduce the irritation associated with personal care compositions, at least in part, by preferentially forming larger micelles (which tend to be less irritating) than traditional surfactants. Polymerized surfactants suitable for use in the present invention include polymerized surfactants of various chemical classifications and obtained via a variety of synthetic routes. Examples include polymers having a backbone that substantially comprises a plurality of carbon-carbon bonds, preferably essentially consists or consists only of carbon-carbon bonds and polymers having a backbone comprising a plurality of carbon-heteroatom bonds (as will be recognized by those of skill in the art, the backbone refers generally to the portion of repeat units in a polymer that is covalently bonded to adjacent repeat units (vs. "pendant groups")). Examples of suitable polymers having a backbone consisting essentially of carbon-carbon bonds and polymers comprising carbon-heteroatom bonds include the following, as well as, combinations of two or more thereof, and the like:

[I.] Polymers having a backbone that substantially comprises carbon-carbon bonds such as may be (1) formed from ethylenically (or acetylenically) unsaturated monomers or (2) polyketones (in all subclasses-(A)-(D) hereunder, n=7 to 2,000 and m is up to 10,000):

Subclass (A): Homopolymerization of prefabricated reactive amphiphiles containing ethylenically unsaturated functionalities (hereinafter "EUAHs").

where $R_1=R_2=H$, $R_3=H$ or $CH_3$, and $R_4$ comprises Amphiphilic (Amphil) group, or where $R_1=R_2=H$, $R_3$ comprises a hydrophilic group-(Hphil), and $R_4$ comprises hydrophobic group (Hphob), or where $R_1$, $R_3$ are independently H or $CH_3$, $R_2$ comprises Hphil, and $R_4$ comprises Hphob group, or where $R_1$, $R_4$ are independently H or $CH_3$, $R_3$ comprises Hphil, and $R_4$ comprises Hphob group, or where $R_2$, $R_3$ are independently H or $CH_3$, $R_1$ comprises Hphil, and $R_4$ comprises Hphob group to yield a polymerized surfactant with an amphiphilic repeat unit shown in brackets immediately below, and having a number of amphiphilic repeat units, n:

Examples of monomers useful for making this class of polymerized surfactants include:

Anionic:
  ω-alkeneoates: e.g. sodium 11-undecenoate where $R_1$=any linear or branched carbon chain containing more than 5 carbon atoms and $M=H^+$, $NH_4^+$, or any Group IA alkali-metal cation.
  (Meth)acrylamidoalkylcarboxylates and (meth)acryloyloxyalkylcarboxylates: e.g. sodium 11-acrylamidoundecanoate, sodium 11-methacryloyloxyundecanoate where $R_2$=H or $CH_3$, X=O or NH, $R_3$=any linear or branched carbon chain-containing more than 5 carbon atoms and $M=H^+$, $NH_4^+$, or any Group IA alkali metal cation.

(Meth)acrylamidoalkylsulfonic acids: e.g. 2-acrylamidododecylsulfonic acid where $R_4$=H or $CH_3$, X=O or NH, $R_5$=any linear or branched carbon chain containing more than 5 carbon atoms and $M=H^+$, $NH_4^+$, or any Group IA alkali metal cation.

Allylalkylsulfosuccinates: e.g. sodium allyldodecylsulfosuccinate (TREM LF-40, Cognis)

where $R_6$=any linear or branched carbon chain containing more than 5 carbon atoms and $M=H^+$, $NH_4^+$, or any Group-IA alkali metal cation.

Cationic:
  Quaternized aminoalkyl(meth)acrylamides and aminoalkyl(meth)acrylates: e.g. (3-methacrylamidopropyl)dodecyldimethylammonium chloride (2-methacryloyloxyethyl)dodecyl dimethylammonium chloride where $R_7$=H or $CH_3$, X=O or NH, $R_8$=any linear or branched carbon chain containing 5 or less carbon atoms, $R_9$=H, $CH_3$, $CH_2CH_3$ or $CH_2CH_2OH$, $R_{10}$=any linear or branched carbon chain containing more than 5 carbon atoms and Z=any Group VII-A halide anion, OR
where $R_7$=H or $CH_3$, X=O or NH, $R_8$=any linear or branched carbon chain containing more than 5 carbon atoms, $R_9$, $R_{10}$ are independenly H, $CH_3$, $CH_2CH_3$ or $CH_2CH_2OH$, and Z=any Group VII-A halide anion Quaternized vinylpyridines: e.g. (4-vinyl)dodecylpyridinium bromide where $R_{11}$=any linear or branched carbon chain containing more than 5 carbon atoms and Z=any Group VII-A halide anion.

Alkyldiallylmethylammonium halides: e.g. diallyidodecylmethylammonium chloride where $R_{12}$=H, $CH_3$ or $R_{13}$, $R_{13}$=any linear or branched carbon chain containing more than 5 carbon atoms and Z=any Group VII-A halide anion.

Zwitterionic:

Ammonioalkanecarboxylates: e.g. 2-[(11-(N-methylacrylamidyl)undecyl)dimethylammohio]acetate where $R_{14}$=H or $CH_3$, X=O or N, $R_{15}$=H, $CH_3$, $CH_2CH_3$ or $CH_2CH_2OH$, $R_{16}$=any linear or branched carbon chain more than 5 carbon atoms, $R_{17}$=any linear or branched carbon chain containing 5 or less carbon atoms, and $R_{18}$=H, $CH_3$, or nothing.

Ammonioalkanesulfonates: e.g. 3-[(11-methacryloyloxyundecyl)dimethylanmmonio]propanesulfonate where $R_{19}$=H or $CH_3$, X=O or N, $R_{20}$=H, $CH_3$, $CH_2CH_3$ or $CH_2CH_2OH$, $R_{21}$=any linear or branched carbon chain more than 5 carbon atoms, $R_{22}$=any linear or branched carbon chain containing 5 or less carbon atoms, and $R_{23}$=H, $CH_3$, or nothing.

Nonionic:

ω-methoxypoly(ethyleneoxy)alkyl-α-(meth)acrylates:
e.g. ω-methoxypoly(ethyleneoxy)undecyl-α-methacrylate where $R_{24}$=H or $CH_3$, X=O, $R_{25}$=any linear or branched carbon chain more than 5 carbon atoms, n is an integer from about 4 to about 800, and $R_{26}$=any linear or branched carbon chain containing 5 or less carbon atoms ω-alkoxypoly(ethyleneoxy)-α-(meth)acrylates and ω-alkoxypoly(ethyleneoxy)-α-itaconates: e.g. steareth-20 methacrylate, ceteth-20 itaconate where $R_{27}$=H, $CH_3$, or $CH_2COOH$, X=O, $R_{28}$=any linear or branched carbon chain more than 5 carbon atoms, and n is an integer from about 4 to about 800

Sublclass (B): Copolymerization of one or more prefabricated reactive amphiphiles containing ethylenically unsaturated functionalities from above with another reactive amphiphilie from subclass (A) above and/or with one or more ethylenically unsaturated hydrophilic comonomers of the formula hereinafter "EUACs":

where $R_5$=$R_6$=H, $R_7$=H or $CH_3$, and $R_8$ comprises HPhil group, or where $R_5$, $R_6$ are independently H or $CH_3$, $R_7$ comprises HPhil group, and $R_8$ comprises HPhil group.

where $R_5$, $R_7$ are independently H or $CH_3$, $R_6$ comprises HPhil group, and $R_8$ comprises HPhil group where $R_6$, $R_7$ are independently H or $CH_3$, $R_5$ comprises HPhil group, and $R_8$ comprises HPhil group to yield a polymerized surfactant with an amphiphilic repeat unit shown in brackets immediately below, and having a number of amphiphilic repeat units, n and a number of non-amphiphilic repeat units, m:

Examples of prefabricated reactive amphiphiles containing ethylenically unsaturated functionalities are described above with reference to (A). Examples of hydrophilic comomomers that may reacted therewith include:

i) Nonionic: acrylamide, N,N-dimethylacrylamide, N-vinylformamide, hydroxyethyl(meth)acrylate, glyceryl methacrylate, sucrose mono(meth)acrylate, ω-methoxypoly(ethyleneoxy)-α-(meth)acrylate ii) Anionic: acrylic acid, 2-acrylamido-2-methylpropanesulfonic acid, 3-acrylamido-3-methylbutanoic acid iii) Cationic: N,N-dimethylaminoethyl methacrylate, N,N-dimethylpropyl (meth)acrylamide, (3-(meth)acrylamidopropyl)trimethylammonium chloride, diallyldimethylammonium chloride iv) Zwitterionic: 3-[(3-(meth)acrylamidopropyl)dimethylammonio]propanesulfonate, 3-(3-(meth)acrylamidopropyldimethylammonio)propionate, 3-(3-(meth)acrylamidopropyldiriethylammonio)acetate Subclass (C): Polymerization of multifunctional amphiphilic molecules with multifunctional linking agents (for example, the step-growth polymerization of alkyl(poly)glucosides with difunctional linkers such as dicarboxylic acids, bis(acyl halide)s, diisocyanates, bis(epoxide)s, or epichlorihydrin) yielding a polymerized surfactant with an amphiphilic repeat unit shown in brackets below, and having a number of amphiphilic repeat units, n (hereinafter "step-growth amphiphiles" or "SGAs"):

Subclass (D): Post-polymerization modification of precursor polymers to render some or all repeat units amphiphilic; yielding a polymerized surfactant with an amphiphilic repeat unit shown in brackets below, and having a number of amphiphilic repeat units, n and a number of non-amphiphilic repeat units, m (hereinafter "PPDAs"):

Examples are indicated below:

v) Via post-polymerization modification to render repeat units amphiphilic:

(a) Hydrolysis of 1:1 alternating copolymers of maleic anhydride and long chain α-olefins or alkyl vinyl ethers (b) Ring-opening of 1:1 alternating copolymers of maleic anhydride and long chain α-olefins or alkyl vinyl ethers with aminoalkylsulfonic acids, aminoalkylcarboxylic acids or dialkylaminoalkylamines vi) Via post-polymerization modification to incorporate amphiphilic repeat units:

(a) Reaction of polymer with repeat units comprising hydroxyl functionalities, such as polyvinylalcohol, hydroxyethylcellulose, or dextran, with 3-chloro-2-hydroxypropylalkyldimethylammonium chlorides, such as QUAB 342, 360, and 426 commercially available from Degussa AG of Parsippany, N.J.

(b) Partial quaternization of poly(4-vinylpyridine) with alkylbromides

Examples of suitable polymerized surfactants having a backbone comprised of carbon-heretoatom bonds include SGAs and PPDAs having such a backbone, such as, polyethers, including polysaccharides, polyesters, polycarbohates, polyanhydrides, polyamides, polyurethanes, polyureas, polyimides, polysulfones, polysulfides, combinations of two or more thereof, and the like.

According to certain preferred embodiments, the polymerized surfactant for use in the present invention comprise EUAHs, such as Poly (sodium allyldodecylsulfosuccinate), and the like, EUACs, such as Poly(acrylic acid co-2-acrylamideododecylsulfonic acid), Poly (sodium allyldodecyl sulfosuccinate-co-acrylic acid), and the like, carbon-carbon backbone PPDA polymers such as octadecene/maleic anhydride copolymers, tetradecene/maleic anhydride copolymers, derivatives thereof (including, for example, hydrolyzed derivatives, amidated derivatives, and the like), combinations of two or more thereof, and the like.

In certain other preferred embodiments, the polymerized surfactants for use in the invention comprise carbon-heteroatom backbone polymers, such as, polysaccharides, polyesters, polycarbonates, polyanhydrides, polyamides, polyurethanes, polyureas, polyimides, polysulfones, polysulfides, combinations of two or more thereof. Certain preferred carbon-heteroatom backbone polymers include polysaccharides.

The molecular weight of the polymerized surfactant is not critical. In one embodiment of the invention, the polymerized surfactant has a molecular weight from about 3500 to about 500,000. In a preferred embodiment, the polymerized surfactant has a molecular weight from about 5000 to about 200,000, more preferably from about 7500 to about 100,000, and most preferably from about 10,000 to about 50,000.

Any amounts of polymerized surfactants suitable to produce micelle size distributions of the present invention may be combined according to the present methods. According to certain embodiments, polymerized surfactant is used in a concentration from greater than about 0.1% to about 30% by weight of active polymerized surfactant in the composition. Preferably, polymerized surfactant is in a concentration from about 0.5 to about 20%, more preferably from about 1 to about 15%, even more preferably from about 2 to about 10% of active polymerized surfactant in the composition. In certain other preferred embodiments, the compositions of the present invention comprise from about 0.5 to about 15%, more preferably from about 1.5 to about 10%, even more preferably from about 2 to about 7%, even more preferably from about 3 to about 7% of active polymerized surfactant in the composition.

Compositions useful in the present invention may also include any of a variety of monomeric surfactants. By "monomeric surfactants" it is meant any surface active agents that do not meet the definition of "polymerized surfactant" as defined above. The monomeric surfactants may be anionic, nonionic, amphoteric or cationic, examples of which are detailed below.

According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

alkyl sulfates of the formula

R'—CH$_2$OSO$_3$X';

alkyl ether sulfates of the formula

R'(OCH$_2$CH$_2$)$_v$OSO$_3$X';

alkyl monoglyceryl ether sulfates of the formula

R'OCH$_2$CHCH$_2$OSO$_3$X';
|
OH alkyl monoglyceride sulfates of the formula

R'CO$_2$CH$_2$CHCH$_2$OSO$_3$X';
|
OH alkyl monoglyceride sulfonates of the formula

R'CO$_2$CH$_2$CHCH$_2$SO$_3$X';
|
OH alkyl sulfonates of the formula

R'—SO$_3$X';

alkylaryl sulfonates of the formula alkyl sulfosuccinates of the formula:

alkyl ether sulfosuccinates of the formula:

alkyl sulfosuccinamates of the formula:

alkyl amidosulfosuccinates of the formula alkyl carboxylates of the formula:

R'—(OCH$_2$CH$_2$)$_w$—OCH$_2$CO$_2$X';

alkyl amidoethercarboxylates of the formula:

alkyl succinates of the formula:

fatty acyl sarcosinates of the formula:

fatty acyl amino acids of the formula:

fatty acyl taurates of the formula:

fatty alkyl sulfoacetates of the formula:

alkyl phosphates of the formula:

wherein
R' is an alkyl group having from about 7 to about 22, and preferably from about 7 to about 16 carbon atoms,
$R'_1$ is an alkyl group having from about 1 to about 18, and preferably from about 8 to about 14 carbon atoms,
$R'_2$ is a substituent of a natural or synthetic I-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
v is an integer from 1 to 6;
w is an integer from 0 to 20;
and mixtures thereof.

Any of a variety of nonionic surfactants are suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester. Examples of such preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from Uniqema of Chicago, Ill. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose polymer and is available commercially from Cognis Corporation of Ambler, Pa. under the tradename, "Plantaren 2000."

Any of a variety of amphoteric surfactants are suitable for use in the present invention. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in the present invention include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

wherein
A is an alkyl or alkenyl group having from about 7 to about 21, e.g. from about 10 to about 16 carbon atoms;
x is an integer of from about 2 to about 6;
$R_5$ is hydrogen or a carboxyalkyl group containing from about 2 to about 3 carbon atoms;
$R_6$ is a hydroxyalkyl group containing from about 2 to about 3 carbon atoms or is a group of the formula:

wherein
$R_8$ is an alkylene group having from about 2 to about 3 carbon atoms and n is 1 or 2; and
$R_7$ is a carboxyalkyl group containing from about 2 to about 3 carbon atoms;

Examples of suitable alkyl betaines include those compounds of the formula:

wherein
B is an alkyl or alkenyl group having from about 8 to about 22, e.g., from about 8 to about 16 carbon atoms;
$R_9$ and $R_{10}$ are each independently an alkyl or hydroxyalkyl group having from about 1 to about 4 carbon atoms; and
p is 1 or 2.

A preferred betaine for use in the present invention is lauryl betaine, available commercially from Albright & Wilson, Ltd. of West Midlands, United Kingdom as "Empigen BB/J."

Examples of suitable amidoalkyl betaines include those compounds of the formula wherein
D is an alkyl or alkenyl group having from about 7 to about 21, e.g. from about 7 to about 15 carbon atoms;
$R_{11}$ and $R_{12}$ are each independently an alkyl or Hydroxyalkyl group having from about 1 to about 4 carbon atoms;
q is an integer from about 2 to about 6; and m is 1 or 2.

One amidoalkyl betaine is cocamidopropyl betaine, available commercially from Degussa Goldschmidt Chemical Corporation of Hopewell, Va. under the tradename, "Tegobetaine L7."

Examples of suitable amidoalkyl sultaines include those compounds of the formula wherein
E is an alkyl or alkenyl group having from about 7 to about 21, e.g. from about 7 to about 15 carbon atoms;
$R_{14}$ and $R_{15}$ are each independently an alkyl, or hydroxyalkyl group having from about 1 to about 4 carbon atoms;
r is an integer from about 2 to about 6; and
$R_{13}$ is an alkylene or hydroxyalkylene group having from about 2 to about 3 carbon atoms;

In one embodiment, the amidoalkyl sultaine is cocamidopropyl hydroxysultaine, available commercially from Rhodia Inc. of Cranbury, N.J. under the tradename, "Mirataine CBS."

Examples of suitable amphophosphate compounds include those of the formula:

wherein
G is an alkyl or alkenyl group having about 7 to about 21, e.g. from about 7 to about 15 carbon atoms;
s is an integer from about 2 to about 6;
$R_{16}$ is hydrogen or a carboxyalkyl group containing from about 2 to about 3 carbon atoms;
$R_{17}$ is a hydroxyalkyl group containing from about 2 to about 3 carbon atoms or a group of the formula:

wherein
$R_{19}$ is an alkylene or hydroxyalkylene group having from about 2 to about 3 carbon atoms and t is 1 or 2; and
$R_{18}$ is an alkylene or hydroxyalkylene group having from about 2 to about 3 carbon atoms.

In one embodiment, the amphophosphate compounds are sodium lauroampho PG-acetate phosphate, available commercially from Uniqema of Chicago, Ill. under the tradename, "Monateric 1023," and those disclosed in U.S. Pat. No. 4,380,637, which is incorporated herein by reference.

Examples of suitable phosphobetaines include those compounds of the formula:

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

wherein
I is an alkyl or alkenyl group containing from about 8 to about 22, e.g. from about 8 to about 16 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4.

Classes of cationic surfactants that are suitable for use in this invention include alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

Any amounts of monomeric surfactant suitable to produce low small micelle fraction composition may be combined according to the present methods. For example, the amount of monomeric surfactants used in the present invention may be from about 0.1 to about 30%, more preferably from about 0.5 to about 20%, even more preferably from about 1 to about 15% of total active monomeric surfactant in the composition, and even more preferably from about 2% to about 10%.

Any relative amounts of polymerized surfactants and monomeric surfactant suitable to produce low small micelle fraction composition may be combined according to the present methods. According to certain embodiments, the compositions comprise a ratio of polymerized surfactant to sum total of all monomeric surfactants of from about 0.1:1 to about 5:1, and preferably from about 0.25:1 to about 3:1.

In addition to monomeric surfactants, the compositions of the present invention may comprise any of a variety of additional other ingredients used conventionally in personal care compositions ("personal care components"). These other ingredients nonexclusively include one or more, pearlescent or opacifying agents, thickening agents, emollients, secondary conditioners, humectants, chelating agents, actives, exfoliants, and additives which enhance the appearance, feel and fragrance of the compositions, such as colorants, fragrances, preservatives, pH adjusting agents, and the like.

Any of a variety of commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent may be present in an amount, based upon the total weight of the composition, of from about 1 percent to about 10 percent, e.g. from about 1.5 percent to about 7 percent or from about 2 percent to about 5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty-acids having from about 16 to about 22 carbon atoms (b) a polyalkylene glycol of the formula: HO-(JO)$_a$—H, wherein J is an alkylene group having from about 2 to about 3 carbon atoms; and a is 2 or 3; fatty alcohols containing from about 16 to about 22 carbon atoms; fatty esters of the formula: KCOOCH$_2$L, wherein K and L independently contain from about 15 to about 21 carbon atoms; inorganic solids insoluble in the shampoo composition, and mixtures thereof.

The pearlescent or opacifying agent may be introduced to the mild cleansing composition as a pre-formed, stabilized aqueous dispersion, such as that commercially available from Cognis Corporation of Ambler, Pa. under the tradename, "Euperlan PK-3000." This material is a combination of glycol disteirate (the diester of ethylene glycol and stearic acid), Laureth-4 (CH$_3$(CH$_2$)$_{10}$CH$_2$(OCH$_2$CH$_2$)$_4$OH) and cocamidopropyl betaine and may be in a weight percent ratio of from about 25 to about 30: about 3 to about 15: about 20 to about 25, respectively.

Any of a variety of commercially available thickening agents, which are capable of imparting the appropriate viscosity to the personal cleansing compositions are suitable for use in this invention. If used, the thickener may, for example, be present in an amount sufficient to raise the Brookfield viscosity of the composition to a value of between about 500 to about 10,000 centipoise. Examples of suitable thickening agents nonexclusively include: mono or diesters of 1) polyethylene glycol of formula: HO—(CH$_2$CH$_2$O)$_z$H, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; hydrophobically-modified alkali swellable emulsions (HASEs); hydrophobically-modified ethoxylated urethanes (HEURs); xantham and guar gums; and mixtures thereof. Preferred thickeners include polyethylene glycol ester, and more preferably PEG-150 disteirate which is available from the Stepan Company of Northfield, Ill. or from Comiel, S.p.A. of Bologna, Italy under the tradename, "PEG 6000 DS".

Any of a variety of commercially available secondary conditioners, such as volatile silicones, which impart additional attributes, such as gloss to the hair are suitable for use in this invention. The volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethlylcyclosiloxane available commercially from Dow Corning Corporation of Midland, Mich. under the tradename, "DC-345" and mixtures thereof, and preferably include cyclomethicone fluids. Other suitable secondary conditioners include cationic polymers, including polyquarterniums, cationic guar, and the like.

Any of a variety of commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, polyglycerols, and mixtures thereof; 2)polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula CH$_3$—C$_6$H$_{10}$O$_5$—(OCH$_2$CH$_2$)$_c$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA", and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include, for example, parabens, quaternary ammonium species, phenoxyethanol, benzoates, DMDM hydantoin, and are present in the composition in an amount, based upon the total weight of the composition, from about 0 to about 1 percent or from about 0.05 percent to about 0.5 percent.

The polymerized surfactant, optional monomeric surfactants and optional other components of the composition may be combined according to the present invention via any conventional methods of combining two or more fluids or solids. For example, one or more compositions comprising, consisting essentially of, or consisting of at least one polymerized surfactant and one or more compositions comprising, consisting essentially of, or consisting of water, monomeric surfactants or suitable ingredients may be combined by pouring, mixing, adding dropwise, pipetting, pumping, and the like, one of the compositions comprising the polymerized surfactant into or with the other in any order using any conventional equipment such as a mechanically stirred propeller, paddle, and the like.

The methods of the present invention may further comprise any of a variety of steps for mixing or introducing one or more of the optional components described hereinabove with or into a composition comprising a polymerized surfactant either before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising the polymerized surfactant.

The pH of the present compositions is not critical, but may be in a range that does not facilitate irritation to the skin, such as from about 5 to about 7. The viscosity of the personal care composition is not critical, although may be a spreadable cream or lotion or gel.

The present compositions may be of varying phase compositions, but are preferably aqueous solutions or otherwise include an exterior aqueous phase (e.g., aqueous phase is the most exterior phase of the composition). As such, compositions of the present invention may be formulated to be oil-in-water emulsions that are shelf-stable in that the emulsion does not lose phase stability or "break" when kept at standard conditions (22 degrees Celsius, 50% relative humidity) for a week or more after it is made.

In certain embodiments, the compositions produced via the present invention are preferably used as or in personal care products for treating or cleansing at least a portion of the human body. Examples of certain preferred personal care products include various products suitable for application to the skin, hair, and/or vaginal region of the body, such as shampoos, hand, face, and/or body washes, bath additives, gels, lotions, creams, and the like. As discussed above, applicants have discovered unexpectedly that the instant methods provide personal care products having-reduced irritation to the skin and/or eyes and, in certain embodiments one or more of desirable properties such as foaming characteristics, rheology, and functionality, even at high surfactant concentrations.

The present invention provides methods of treating and/or cleansing the human body comprising contacting at least a portion of the body with a composition of the present invention. Certain preferred methods comprising contacting mammalian skin, hair and/or vaginal region with a composition of the present invention to cleanse such region and/or treat such region for any of a variety of conditions including, but not limited to, acne, wrinkles, dermatitis, dryness, muscle pain, itch, and the like. In certain preferred embodiments, the contacting step comprises applying a composition of the present invention to human skin, hair or vaginal region.

The cleansing methods of the present invention may further comprise any of a variety of additional, optional steps associated conventionally with cleansing hair and skin including, for example, lathering, rinsing steps, and the like.

EXAMPLES

The following Trans-Epithelial Permeability ("TEP"), Dynamic Light Scattering, and Foam tests are used in the instant methods and in the following Examples. In particular, as described above, the TEP test is used to determine when a composition is a reduced irritation composition according to the present invention; the Dynamic Light Scattering test may be used to determine the suitability of a particular polymerized surfactant (e.g., PMOD %) or composition (e.g., CMID %); and the Foam test may be used to determine the propensity of compositions to provide the high levels of foam, often desirable for cleansing compositions.

Unless otherwise indicated, the amounts of ingredients in the Example and Comparative compositions listed in the tables are expressed in w/w % of ingredient based on the total composition.

Trans-Epithelial Permeability Test ("TEP Test"):

Irritation to the eyes and/or skin expected for a given formulation is measured in accordance with the Invittox Protocol Number 86, the "Trans-epithelial Permeability (TEP) Assay" as set forth in Invittox Protocol Number 86 (May 1994), incorporated herein by reference. In general, the ocular and/or skin irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

Dynamic Light Scattering Test ("DLS Test"):

Dynamic light scattering (DLS, also known as Photon Correlation Spectroscopy or PCS) is a well-known method for determination of average micelle size (measured as hydrodynamic diameter, $d_H$) and micelle size distribution (A comprehensive explanation of the technique can be found in the ISO test method ISO13321:1996(E). The hydrodynamic size measured by DLS is defined as the size of a hypothetical hard sphere that diffuses in the same, fashion as that of the particle being measured. In practice, micellar species are dynamic (tumbling), solvated species that maybe isotropic (spherical) or anisotropic (e.g. ellipsoidal or cylindrical) in shape. Because of this, the diameter calculated from the diffusional properties of the micelle will be indicative of the apparent size of the dynamic hydrated/solvated particle; hence the terminology, "hydrodynamic diameter." Micellar solutions for determination of micelle $d_H$ are prepared by diluting the compositions to 3.0% of their original concentration with 0.1 μm-filtered deionized water, obtained from a Millipore-Q filtration system. (The target dilution of 3.0% is chosen because it is within the typical concentration range of 1.0%-10% dilution that is encountered during the use of rinse-off personal care compositions. The target dilution is also within the range of dilutions employed in the TEP test.) The samples are agitated on a vortex mixer at 1000 rpm for a minimum of five minutes and then allowed to stand overnight prior to analysis. Samples are passed through a 0.2 μm Anatop-Plus syringe filter into dust-free disposable acrylic sizing cuvettes and sealed.

The samples are analyzed using a Zetasizer Nano ZS DLS instrument (Malvern Instruments, Inc., Southborough, Mass.) operating at 25.0° C. Samples must yield a minimum count rate of 100,000 counts per second (cps) for accurate determination of micelle $d_H$ and micelle size distribution. For samples with count rates below this minimum, the sample concentration maybe be gradually increased (i.e. diluted less) until the minimum count rate is achieved, or in some cases, the sample may be run in neat form. Values of micelle $d_H$ and the micelle size distribution are calculated using the Dispersion Technology Software (DTS) v4.10 package (Malvern Instruments Inc., Southborough, Mass.), which calculates the Z-average micelle $d_H$ according to the ISO13321 test method. Values of average micelle $d_H$ are reported herein as the Z-average micelle $d_H$. The reported values of micelle $d_H$ are the average of three individual measurement runs. The intensity distribution of micelle size calculated by the DTS software is used to calculate the fraction of micelles having values of $d_H$ under a given size limit.

Additives exhibiting relatively large values of $d_H$ (i.e. greater than about 200 nm) compared to micellar species, for example, high MW polymeric rheology modifiers, polymeric conditioners, particulate opacifiers, (micro)emulsions of hydrophobic emollients, silicone (micro)emulsions, etc., are routinely added to personal care compositions comprising micellar species. To those skilled in the art of DLS, it is apparent that such noamicellar materials will exhibit light scattering intensities orders of magnitude greater than the relatively smaller micellar species in the diluted sample. The scattering intensity of such materials will overwhelm the scattering signal of the micellar species, thus interfering in the accurate determination of micelle $d_H$. Typically, this type of interference will lead to an erronously large measured value of micelle $d_H$. To avoid such interference, it is most preferable to measure the micelle $d_H$ of the composition in the absence of additives exhibiting values of $d_H$ greater than about 200 nm. Those skilled in the art of DLS will recognize that additives exhibiting large values of $d_H$ should be separated from the sample via filtration or ultracentrifugation prior to determination of the micelle $d_H$ of the sample. Alternatively, higher order analysis of the DLS data using the Dispersion Technology Software v4.10 package may also be employed to obtain enhanced resolution and properly characterize micelle $d_H$ in the presence of nonmicellar scattering species.

In accord with the above description and as shown hereafter in the Examples, the "PMOD %" and "PMODz-average" associated with a polymerized surfactant are calculated by preparing a model composition comprising about 4.8 active weight % of the polymerized surfactant, 0.3 weight percent of a combination of sodium methyl- (and) sodium propyl- (and) sodium ethyl paraben, (such as the product commercially available as Nipasept Sodium), 0.25 weight percent of tetrasodium EDTA (such as Versene 100 XL), with q.s. water, and using the DLS test to measure the fraction of micelles having a dH of less than 9 nm in the resulting model composition (PMOD %), and the z-average micelle dH associated therewith (PMODz-average). Applicants have recognized that in certain embodiments, the polymerized surfactant to be tested may be incompatible with the above model composition. Thus, if, and only if, the formulation of the above model composition results in two separate liquid phases and/or precipitation of the polymer surfactant, then the PMOD % and PMODz-average procedure comprises making a composition comprising about 4.8 active weight % of the polymerized surfactant, 0.5 weight percent of sodium benzoate, 0.25 weight percent of tetrasodium EDTA (such as Versene 100 XL), with q.s. citric acid to a pH of 4.8±0.2, with q.s. water, and using the DLS test to measure the fraction of micelles having a $d_H$ of less than 9 nm in the resulting model composition (PMOD %), and the z-average micelle $d_H$ associated therewith (PMODz-average).

For any other composition (including non-model compositions), the fraction of micelles having a $d_H$ of less than 9 nm (CMID %) and the z-average micelle $d_H$ (CMIDz-average) associated therewith are measured using the DLS test for such composition.

Foam Volume Evaluation ("Foam Test"):

The following Foam Test was performed on various personal care compositions to determine the Maximum Foam Volume upon agitation according to the present invention. The procedure was accomplished by adding 5.0 grams of the model solution that included a particular polymerized surfactant to be tested, to 995 grams of deionized water and mixing until homogenous. The mixture was then added toga sample tank of a Sita R-2000 foam tester (commercially available from Future Digital Scientific, Co.; Bethpage, N.Y.). The test parameters were set to repeat three runs (series count=3) of 250 ml sample size (fill volume=250 ml) with twelve stir cycles (stir count=12) for a 15 second stir time per cycle (stir time=15 seconds) with the rotor spinning at 1000 RPM (revolution=1000) at a temperature setting of 30° C.±2° C. Foam Volume data was collected at each stir cycle and the average and standard deviation of the three runs was determined. Maximum Foam Volume was reported for each Example as the value after the twelfth stir cycle.

Examples E1-E8

Preparation of Model Compositions

The model compositions of Examples E1 through E8 were prepared by blending a particular surfactant with other ingredients according to the materials and amounts listed in Table 1:

TABLE 1

| Tradename | INCI Name | E1 | E2 | E3 | E4 | E5 | E6 | E7 | E8 |
|---|---|---|---|---|---|---|---|---|---|
| PA-18, hydrolyzed (26%) | Hydrolyzed Octadecene/MA Copolymer (prop.) | 18.46 | — | — | — | — | — | 48.00 | — |
| PA-14, hydrolyzed (26%) | Hydrolyzed Tetradecene/MA Copolymer (prop.) | — | 18.46 | — | — | — | — | — | 12.00 |
| PAT-18 (17%) | Sodium Taurate Amide of Octadecene/MA Copolymer (prop.) | — | — | 28.24 | — | — | — | — | — |
| PAT-14 (14%) | Sodium Taurate Amide of Tetradecene/MA Copolymer (prop.) | — | — | — | 34.29 | — | — | — | — |

TABLE 1-continued

| Tradename | INCI Name | E1 | E2 | E3 | E4 | E5 | E6 | E7 | E8 |
|---|---|---|---|---|---|---|---|---|---|
| Poly(acrylic acid-co-2-acrylamidododecylsulfonic acid) (9%) | Acrylates/Acryloyldecyltaurine Copolymer (prop.) | — | — | — | — | 53.33 | — | — | — |
| Poly(sodium allyldodecyl-sulfosuccinate-co-acrylic acid) (11%) | Acrylates/Sodium Allyldodecylsulfosuccinate Copolymer (prop.) | — | — | — | — | — | 46.64 | — | — |
| Poly(sodium allyldodecyl-sulfosuccinate) (10%) | Poly(Sodium Allyldodecylsulfosuccinate) (prop.) | — | — | — | — | — | — | 48 | — |
| PolySugaNate 100P (40%) | Poly(Decylglucosides Hydroxypropylsulfonate) | — | — | — | — | — | — | q.s. | 12.00 |
| Nipasept Sodium | Sodium Methyl- (and) Sodium Propyl- (and) Sodium Ethylparaben | 0.30 | 0.30 | 0.30 | 0.30 | 0.30 | 0.30 | 0.30 | 0.30 |
| Versene 100XL | Tetrasodium EDTA | 0.25 | 0.25 | 0.25 | 0.25 | 0.25 | 0.25 | 0.25 | 0.25 |
| Sodium Hydroxide solution (20%) | Sodium Hydroxide | q.s. | q.s. | q.s. | q.s. | q.s. | q.s. | q.s. | q.s. |
| Citric Add solution (20%) | Citric Acid | q.s. | q.s. | q.s. | q.s. | q.s. | q.s. | q.s. | q.s. |
| Purified Water | Water | q.s. | q.s. | q.s. | q.s. | q.s. | q.s. | q.s. | q.s. |

The low-DP polymerized surfactants noted in Table 1 were prepared as follows: PA-18, hydrolyzed, of Example E1 was obtained by performing a reaction of a 1:1 alternating copolymer of 1-octadecene and maleic anhydride (PA-18 Low Viscosity Low Color grade, commercially available from Chevron Phillips Chemical, LLC) with sodium hydroxide in aqueous solution to yield a octadecene/MA copolymer having an average of approximately 25-75 amphiphilic repeat units on a weight average basis, a mole fraction of amphiphilic repeat units of about 100%, and a hydrophobic group of C16 within the amphiphilic repeat unit.

PA-14, hydrolyzed, of Example E2 was obtained by performing a reaction of a 1:1 alternating copolymer of 1-tetradecene and maleic anhydride (PA-14) with sodium hydroxide in aqueous solution to yield a tetradecene/MA copolymer having a weight average of approximately 25-75 amphiphilic repeat units, a mole fraction of amphiphilic repeat units of about 100%, and a hydrophobic group of C12 within, the amphiphilic repeat unit.

PAT-18, taurine derivative, of Example E3 was obtained via the base-catalyzed reaction of a 1:1 alternating copolymer of 1-octadecene and maleic anhydride (PA-18 Low Viscosity Low Color grade, Chevron Phillips Chemical, LLC of The Woodlands, Tex.) with the aminoalkylsulfonic acid taurine in aqueous solution according to the procedure of Grief, N., et al. (ref. WO9716464A1) to yield a taurate amide of octadecene/MA copolymer having a weight average of approximately 25-75 amphiphilic repeat units, a mole fraction of amphiphilic repeat units of about 100%, and a hydrophobic group of C16 within the amphiphilic repeat unit.

PAT-14, taurine derivative, of Example E4 was obtained via the base-catalyzed reaction of a 1:1 alternating copolymer of 1-tetradecene and maleic anhydride (PA-14) with the aminoalkylsulfonic acid taurine in aqueous solution according to the procedure of Grief, N., et al. (ref. WO9716464A1) to yield a taurate amide of tetradecene/MA copolymer having a weight average of approximately 25-75 amphiphilic repeat units, a mole fraction of amphiphilic repeat units of about 100%, and a hydrophobic group of C12 within the amphiphilic repeat unit.

Poly(acrylic acid co-2-acrylamidododecylsulfonic acid) of Example E5 was prepared via the free-radical copolymerization of acrylic acid and acryloyldecyltaurine in aqueous solution. Acryloyldecyltaurine is prepared according to the procedure of Harrison, K. S. (ref. U.S. Pat. No. 3,544,597). The resulting copolymer had a weight average of approximately 10-500 amphiphilic repeat units, a mole fraction of amphiphilic repeat units of about 50%, and a hydrophobic group of C12 within the amphiphilic repeat unit.

Poly (sodium allyldodecyl sulfosuccinate-co-acrylic acid) of Example E6 was prepared via the free-radical copolymerization of acrylic acid and sodium allyldodecylsulfosuccinate (TREM LF-40, commercially available from Cognis Corporation of Ambler, Pa.) in aqueous media. The resulting copolymer had a weight average of approximately 50-100 amphiphilic repeat units, a mole fraction of amphiphilic repeat units of about 50%, and a hydrophobic group of C12 within the amphiphilic repeat unit.

Poly (sodium allyldodecylsulfosuccinate) of Example E7 was prepared via the free-radical polymerization of sodium allyldodecylsulfosuccinate (TREM LF-40, commercially avaialbe from Cognis Corporation) in aqueous media. The resulting copolymer had a weight average of approximately 10-20 amphiphilic repeat units, a mole fraction of amphiphilic repeat units of about 100%, and a hydrophobic group of C12 within the amphiphilic repeat unit.

PolySuga® Nate 100P of Example E8 was obtained from Colonial Chemical of South Pittsburg, Tenn. under the tradename PolySuga® Nate 100P. Product literature refers to this as a sulfonated poly(alkyl polyglucoside).

The model compositions of Table 1 were prepared as follows: water (about 50.0 parts) was added to a beaker fitted with a mechanical stirrer. Nipasept Sodium powder was added until dissolved. The appropriate surfactant was added also at low stir speed to avoid aeration. Versene was added and mixing was continued. Heat was provided (no greater than 60 C) if necessary to obtain a uniform solution. Batch was allowed to cool to 25 C if necessary, while mixing was continued at medium speed. pH was adusted to 7.0+/−0.2 using citric acid or sodium hydroxide solution. Water was added to q.s. to 100%.

Comparison of Model Compositions: The compositions prepared in accordance with Examples E1-E8 were tested for mildness in accordance with the TEP Test described above. The samples were also tested according to the DLS test. The results of these tests are listed below in Table 2:

TABLE 2

| Example | Polymerized Surfactant | Average TEP Score (%) | Z-Average Micelle $d_H$ (nm), PMOD z-average | Fraction of micelles with $d_H$ < 9 nm, PMOD % |
|---|---|---|---|---|
| E1 | hydrolyzed PA-18 | No leakage | 15.1 | 10% |
| E2 | hydrolyzed PA-14 | No leakage | 48.6[a] | 4% |
| E3 | PAT-18, taurine derivative of PA-18 | 4.85 ± 1.33 | 17.6 | 13% |
| E4 | PAT-14, taurine derivative of PA-14 | No leakage | 13.0[b] | 34% |
| E5 | Poly(acrylic acid-co-2-acrylamidododecylsulfonic acid) (9%) | No leakage | 16.7 | 14% |
| E6 | poly(sodium allyldodecylsulfosuccinate-co-acrylic acid) | No leakage | 8.4[c] | 41% |
| E7 | poly(sodium allyldodecylsulfosuccinate) | 3.72 ± 1.72 | 8.6 | 52% |
| E8 | PolySugaNate 100P | 6.62 ± 0.77 | 8.8 | 53% |

Examples E1 through E7 were also evaluated for foam performance according to the Foam Test described above. The results of these tests are listed below in Table 3:

TABLE 3

| Exampl | Polymerized | Max Foam (mL) |
|---|---|---|
| E1 | hydrolyzed PA- | 73 |
| E2 | hydrolyzed PA- | — |
| E3 | PAT-18, taurine derivative of | 63 |
| E4 | PAT-14, taurine derivative of | 0 |
| E5 | Poly(acrylic acid-co-2-acrylamidododecylsulfonic acid) | 31 |
| E6 | poly(sodium co-acrylic acid | 225 |
| E7 | poly(sodium | 238 |

Comparative Examples C9 C11

Preparation of Model Compositions

Model compositions of Examples C9 through C11 were prepared by mixing a particular surfactant to be evaluated with other ingredients in a manner similar to the model compositions described above (see Examples E1-E8)—and according to the materials and amounts listed in Table 4:

TABLE 4

| Tradename | INCI Name | C9 | C10 | C11 |
|---|---|---|---|---|
| Tegobetaine L7-V (30%) | Cocamidopropyl Betaine | 24.00 | — | — |
| Rhodapex ES-2/K (26%) | Sodium Laureth Sulfate | — | 18.46 | — |
| Cedepal TD403MFLD (30%) | Sodium Trideceth Sulfate | — | — | 16.00 |
| Nipasept Sodium | Sodium Methyl- (and) Sodium Propyl- (and) Sodium Ethylparaben | 0.30 | 0.30 | 0.30 |
| Versene 100XL | Tetrasodium EDTA | 0.25 | 0.25 | 0.25 |
| Sodium Hydroxide solution (20%) | Sodium Hydroxide | q.s. | q.s. | q.s. |
| Citric Acid solution (20%) | Citric Acid | q.s. | q.s. | q.s. |
| Purified Water | Water | q.s. | q.s. | q.s. |

The compositions of Table 4 were prepared as follows: water (50.0 parts) was added to a beaker fitted with a mechanical stirrer. Nipasept Sodium powder was added until dissolved. Monomeric surfactant was slowly added at low stir speed to avoid aeration. Versene was added and mixing was continued. Heat was provided (no greater than 60 C) if necessary to obtain a uniform solution. Batch was allowed to cool to 25 C if necessary, while mixing was continued at medium speed. pH was adusted to 7.0+/−0.2 using citric acid or sodium hydroxide solution. Water was added to q.s. to 100%.

Comparison of Model Compositions: The compositions prepared in accordance with Examples C9-C11 were tested for mildness in accordance with the above TEP Test. The samples were also tested according to the DLS test. The results of these tests are listed below in Table 5:

TABLE 5

| Example | Surfactant | Average TEP Score (%) | Z-Average Micelle $d_H$ (nm), PMOD z-average | Fraction of micelles with $d_H$ < 9 nm, PMOD % |
|---|---|---|---|---|
| C9 | Cocamidopropyl Betaine [a] | 2.55 ± 0.46 | 6.2 | 91% |
| C10 | Sodium Laureth Sulfate | 3.12 ± 0.74 | 2.7 | 100% |
| C11 | Sodium Trideceth Sulfate | 1.73 ± 0.50 | 2.6 | 100% |

As seen in Tables 2 and Table 5 for model compositions tested, it can be see that compositions including low-DP polymerized surfactants that have a PMOD % less than about 90% surprisingly, were generally milder, and often significantly milder when compared with conventional monomeric surfactants that have a PMOD % greater than or equal to about 90%. Also, as shown in Table 3, the model compositions that include polymerized surfactants in most cases are also capable of providing a high level of foam, despite the absence of monomeric surfactant.

Examples E12 E18

Preparation of Cleansing Compositions

The cleansing compositions of Examples E12 through E18 were prepared according to the materials and amounts listed in Table 6:

Comparative Examples C19-C20

Preparation of Cleansing Compositions

The cleansing compositions of Examples C19 and C20 were prepared according to the materials and amounts listed in Table 8.

TABLE 6

| Tradename | INCI Name | E12 | E13 | E14 | E15 | E16 | E17 | E18 |
|---|---|---|---|---|---|---|---|---|
| PA-18, hydrolyzed (26%) | Hydrolyzed Octadecene/MA Copolymer (prop.) | 18.46 | — | — | — | — | — | — |
| PA-14, hydrolyzed (26%) | Hydrolyzed Tetradecene/MA Copolymer (prop.) | — | 18.46 | — | — | — | — | — |
| PAT-18 (17%) | Sodium Taurate Amide of Octadecene/MA Copolymer (prop.) | — | — | 28.24 | — | — | — | — |
| PAT-14 (14%) | Sodium Taurate Amide of Tetradecene/MA Copolymer (prop.) | — | — | — | 34.29 | — | — | — |
| Poly(sodium allyldodecyl-sulfosuccinate) (10%) | Poly(Sodium Allyldodecylsulfosuccinate) (prop.) | — | — | — | — | 48.00 | — | — |
| Poly(sodium allyldodecyl-sulfosuccinate-co-acrylic acid) (11%) | Acrylates/Sodium Allyldodecylsulfosuccinate Copolymer (prop.) | — | — | — | — | — | 46.64 | — |
| PolySugaNate 100P (40%) | Poly(Decylglucosides Hydroxypropylsulfonate) | — | — | — | — | — | — | 12.00 |
| Tegobetaine L7-V (30%) | Cocamidopropyl Betaine | 24.00 | 24.00 | 24.00 | 24.00 | 24.00 | 24.00 | 24.00 |
| Nipasept Sodium | Sodium Methyl- (and) Sodium Propyl- (and) Sodium Ethylparaben | 0.30 | 0.30 | 0.30 | 0.30 | 0.30 | 0.30 | 0.30 |
| Versene 100XL | Tetrasodium EDTA | 0.25 | 0.25 | 0.25 | 0.25 | 0.25 | 0.25 | 0.25 |
| Sodium Hydroxide solution (20%) | Sodium Hydroxide | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. |
| Purified Water | Water | q.s. | q.s. | q.s. | q.s. | q.s. | q.s. | q.s. |

The compositions of Table 6 were prepared as follows: water (about t50.0 parts) was added to a beaker fitted with a mechanical stirrer. Nipasept Sodium powder was added until dissolved. Tegobetaine was added also at low stir speed to avoid aeration. The appropriate polymerized surfactant was then added also at low stir speed to avoid aeration. Versene was added and mixing was continued. Heat was provided (no greater than 60 C) if necessary to obtain a uniform solution. Batch was allowed to cool to 25 C if necessary, while mixing was continued at medium speed. pH was adusted to 7.0+/−0.2 using citric acid or sodium hydroxide solution. Water was added to q.s. to 100%.

Comparison of Cleansing Compositions: The compositions prepared in accordance with Examples E12-E18 were tested for mildness in accordance with the above TEP Test. The samples were also tested according to the DLS test. The results of these tests are listed below in Table 7:

TABLE 8

| Tradename | INCI Name | C19 | C20 |
|---|---|---|---|
| Rhodapex ES-2/K (26%) | Sodium Laureth Sulfate | 18.46 | — |
| Cedepal TD403MFLD (30%) | Sodium Trideceth Sulfate | — | 16.00 |
| Tegobetaine L7-V (30%) | Cocamidopropyl Betaine | 24.00 | 24.00 |
| Nipasept Sodium | Sodium Methyl- (and) Sodium Propyl- (and) Sodium Ethylparaben | 0.30 | 0.30 |
| Versene 100XL | Tetrasodium EDTA | 0.25 | 0.25 |
| Sodium Hydroxide solution (20%) | Sodium Hydroxide | q.s. | q.s. |
| Citric Acid solution (20%) | Citric Acid | q.s. | q.s. |
| Purified Water | Water | q.s. | q.s. |

TABLE 7

| Example | Polymerized Surfactant | TEP Value | Z-Average Micelle $d_H$ (nm), (CMID-Z-AVE.) | Fraction of micelles with $d_H$ < 9 nm, (CMID %.) |
|---|---|---|---|---|
| E12 | hydrolyzed PA-18 | 4.76 ± 0.66 | 13.8 | 10% |
| E13 | hydrolyzed PA-14 | 6.86 ± 0.51 | 17.3 | 4% |
| E14 | PAT-18, taurine derivative of PA-18 | 3.55 ± 0.30 | 12.5 | 23% |
| E15 | PAT-14, taurine derivative of PA-14 | 6.55 ± 0.07 | 12.3 | 24% |
| E16 | poly(sodium allyldodecylsulfosuccinate) | 3.84 ± 0.28 | 19.0 | 4% |
| E17 | poly(sodium allyldodecylsulfosuccinate-co-acrylic acid) | 4.80 ± 1.20 | 6.5 | 80% |
| E18 | PolySugaNate 100P | 2.65 ± 0.26 | 8.5 | 55% |

The compositions of Table 8 were prepared as follows: water (about 50.0 parts) was added to a beaker fitted with a mechanical stirrer. Nipasept Sodium powder was added until dissolved. Tegobetaine was added also at low stir speed to avoid aeration. The appropriate monomeric surfactant (Rhodapex or Cedepal) to be conside-red was then added also at low stir speed to avoid aeration. Versene was added and mixing was continued. Heat was provided (no greater than 60 C) if necessary to obtain a uniform solution. Batch was allowed to cool to 25 C if necessary, while mixing was continued at medium speed. pH was adusted to 7.0+/−0.2 using citric acid or sodium hydroxide solution. Water was added to q.s. to 100%.

Comparison of Cleansing Compositions: The compositions prepared in accordance with Examples C19-C20 were tested for mildness in accordance with the above TEP Test. The samples were also tested according to the DLS test. The results of these tests are listed below in Table 9:

TABLE 9

| Example | Surfactant | TEP Value | Z-Average Micelle $d_H$ (nm), (CMID-Z-AVE.) | Fraction of micelles with $d_H < 9$ nm, (CMID %.) |
|---|---|---|---|---|
| C19 | Sodium Laureth Sulfate | 1.34 ± 0.48 | 5.3 | 94% |
| C20 | Sodium Trideceth | 2.75 ± 0.60 | 5.0 | 94% |

As seen in Tables 7 and Table 9, for compositions tested, it can be see that a variety of polymerized surfactants can be formulated into cleansing compositions that have a surprisingly low small micelle fractions as indicated by CMID % (less than about 90%) when compared to convetional monomeric surfactants. Furthermore, TEP values were surprisingly high for the inventive compositions.

Examples E21-E24

Preparation of Cleansing Compositions

The model compositions of Examples E21 through E24 were prepared according to the materials and amounts listed in Table 10.

TABLE 10

| Tradename | INCI Name | E21 | E22 | E23 | E24 |
|---|---|---|---|---|---|
| PA-18, hydrolyzed (26%) | Hydrolyzed Octadecene/MA Copolymer (prop.) | 18.46 | 18.46 | 18.46 | 18.46 |
| Tegobetaine L7-V (30%) | Cocamidopropyl Betaine | 6.00 | 12.00 | 16.00 | 20.00 |
| Nipasept Sodium | Sodium Methyl- (and) Sodium Propyl- (and) Sodium Ethylparaben | 0.30 | 0.30 | 0.30 | 0.30 |
| Versene 100XL | Tetrasodium EDTA | 0.25 | 0.25 | 0.25 | 0.25 |
| Sodium Hydroxide solution (20%) | Sodium Hydroxide | q.s. | q.s. | q.s. | q.s. |
| Citric Acid solution (20%) | Citric Acid | q.s. | q.s. | q.s. | q.s. |
| Purified Water | Water | q.s. | q.s. | q.s. | q.s. |

The cleansing compositions of Table 10 were prepared in a manner similar to those described for E1-E9 shown in Table 1. The concentration of PA-18, hydrolyzed was held constant.

Comparison of Cleansing Compositions: The compositions prepared in accordance with Examples E21-E24 were tested for mildness in accordance with the above TEP Test. The samples were also tested according to the DLS test. The results of these tests are listed below in Table 11 (Examples E1 and E12 are also shown for comparison):

TABLE 11

| Example | Ratio CAPB:PA-18 | [CAPB] (wt % active) | TEP Value | Z-Average Micelle $d_H$ (nm), (CMID-Z-AVE.) | Fraction of micelles with $d_H < 9$ nm, (CMID %.) |
|---|---|---|---|---|---|
| E1 | 0.00 | 0.0 | No leakage | 15.1 | 10% |
| E21 | 0.38 | 1.8 | No leakage | 19.5 | 3% |
| E22 | 0.75 | 3.6 | No leakage | 20.2 | 3% |

TABLE 11-continued

| Example | Ratio CAPB:PA-18 | [CAPB] (wt % active) | TEP Value | Z-Average Micelle $d_H$ (nm), (CMID-Z-AVE.) | Fraction of micelles with $d_H < 9$ nm, (CMID %.) |
|---|---|---|---|---|---|
| E23 | 1.00 | 4.8 | No leakage | 18.1 | 5% |
| E24 | 1.25 | 6.0 | 5.51 ± 0.20 | 16.2 | 9% |
| E12 | 1.50 | 7.2 | 4.76 ± 0.66 | 13.8 | 18% |

For comparative purposes, compositions with no polymerized surfactant (C9—formula shown in Table 4) or with a monomeric surfactant (SLES) replacing the polymerized surfactant (C19-formula shown in Table 8) are shown below in Table 12:

TABLE 12

| Example | Ratio CAPB:PA-18 | [CAPB] (wt % active) | TEP Value | Z-Average Micelle $d_H$ (nm), (CMID-Z-AVE.) | Fraction of micelles with $d_H < 9$ nm, (CMID %.) |
|---|---|---|---|---|---|
| C9 | (CAPB) no PA-18 | 7.2 | 2.55 ± 0.46 | 6.2 | 91% |
| C19 | (SLES) 1.50 | 7.2 | 1.34 ± 0.48 | 5.3 | 94% |

As seen in Table 11, for compositions tested, it can be see the polymerized surfactant, PA-18, hydrolyzed can be formulated into cleansing compositions with a variety of relative concentration of monomeric surfactant to polymerized surfactant. In each of the examples, the compositions have a surprisingly low small micelle fractions as indicated by CMID % (less than about 90%), especially when compared with similar compositions with conventional surfactants, shown in Table 12.

Examples E25 E27

Preparation of Cleansing Compositions

The cleansing compositions of Examples E25 through E27 were prepared according to the materials and amounts listed in Table 13:

TABLE 13

| Tradename | INCI Name | E25 | E26 | E27 |
|---|---|---|---|---|
| PA-18, hydrolyzed (26%) | Hydrolyzed Octadecene/ MA Copolymer (prop.) | 23.08 | 30.75 | 38.45 |
| Tegobetaine L7-V (30%) | Cocamidopropyl Betaine | 30.00 | 40.00 | 50.00 |
| Nipasept Sodium | Sodium Methyl- (and) Sodium Propyl- (and) Sodium Ethylparaben | 0.30 | 0.30 | 0.30 |
| Versene 100XL | Tetrasodium EDTA | 0.25 | 0.25 | 0.25 |
| Sodium Hydroxide solution (20%) | Sodium Hydroxide | q.s. | q.s. | q.s. |
| Citric Acid solution (20%) | Citric Acid | q.s. | q.s. | q.s. |
| Purified Water | Water | q.s. | q.s. | q.s. |

The cleansing compositions of Table 13 were prepared in a manner similar to those described for E1-E9 shown in Table 1. The ratio of betaine to PA-18, hydrolyzed was held constant.

Comparison of Cleansing Compositions: The compositions prepared in accordance with Examples E25-E27 were tested for mildness in accordance with the above TEP Test. The samples were also tested according to the DLS test. The results of these tests are listed below in Table 14 (Example E12 is also shown for comparison):

TABLE 14

| Example | [PA-18] (wt % active) | [CAPB] + [PA-18] (wt % active) | TEP Value | Z-Average Micelle $d_H$ (hm), (CMID-Z-AVE.) | Fraction of micelles with $d_H < 9$ nm, (CMID %.) |
|---|---|---|---|---|---|
| E12 | 4.8 | 12.00 | 4.76 ± 0.66 | 13.8 | 18% |
| E25 | 6.0 | 15.00 | 3.20 ± 0.25 | 13.8 | 20% |
| E26 | 8.0 | 20.00 | 4.56 ± 0.78 | 13.3 | 25% |
| E27 | 10.0 | 25.00 | 4.00 ± 0.80 | 12.9 | 28% |

As seen in Table 14, for compositions tested, it can be see the polymerized surfactant, PA-18, hydrolyzed can be formulated into cleansing compositions with a variety of total surfactant concentrations (polymerized+monomeric). In each of the examples, the compositions has a surprisingly low small micelle fractions as indicated by CMID % (less than about 90%).

We claim:

1. A method of treating the human body comprising applying to the skin, hair, or vaginal region, a personal care composition comprising a low-DP polymerized surfactant, said composition having a CMID % of less than about 90%.

2. The method of claim 1, wherein said composition has a CMID % of less than about 50%.

3. The method of claim 1, wherein said composition has a TEP value of about 3.5 or greater.

4. The method of claim 1, wherein said composition has a TEP value of at least about of 5 or greater.

5. The method of claim 1 wherein said low-DP polymerized surfactant has a PMOD % of about 90% or less.

6. The method of claim 1 wherein said low-DP polymerized surfactant has a PMOD % of about 80% or less.

7. The method of claim 1 wherein said low-DP polymerized surfactant has a PMOD % of about 50% or less.

8. The method of claim 1 wherein said low-DP polymerized surfactant comprises from about 10 to about 1000 amphiphilic repeat units on a weight average basis.

9. The method of claim 1 wherein said low-DP polymerized surfactant comprises a polymer having a backbone that substantially comprises a plurality of carbon-carbon bonds, wherein said polymer is selected from the group consisting of EUACs, EUAHs, and PPDAs.

10. The method of claim 1 wherein said low-DP polymerized surfactant comprises a polymer having a backbone that substantially comprises a plurality of carbon-heteroatom bonds.

11. The method of claim 10 wherein said low-DP polymerized surfactant is a polysaccharide.

12. The method of claim 1, wherein said composition further comprises at least one surfactant selected from the group consisting of anionic surfactants, amphoteric surfactants, and combinations of two or more thereof.

13. The method of claim 12, wherein said at least one surfactant comprises a betaine.

14. The method of claim 1, wherein said applying step comprises applying an effective amount of such personal care composition to treat a condition selected from the group consisting of acne, wrinkles, dermatitis, dryness, muscle pain, itch.

15. The method of claim 1 wherein said personal care product is a cleanser.

16. A method of making a low-irritation personal care composition comprising combining a low-DP polymerized surfactant with at least one additional personal care component to produce a personal care composition having a CMID % of less than about 90%.

17. The method of claim 16 wherein said personal care composition has a CMID % of less than about 50%.

18. The method of claim 16 wherein said personal care composition has a TEP value of about 3 or greater.

19. The method of claim 16 wherein said low-DP polymerized surfactant has a PMOD % of less than about 90%.

20. The method of claim 16 wherein said low-DP polymerized surfactant has a PMOD % of less than about 80%.

21. The method of claim 16 wherein said low-DP polymerized surfactant comprises a polymer having a backbone that substantially comprises a plurality of carbon-carbon bonds, wherein said polymer is selected from the group consisting of EUACs, EUAHs, and PPDAs.

22. The method of claim 1 wherein said low-DP polymerized surfactant comprises a polymer having a backbone that substantially comprises a plurality of carbon-heteroatom bonds.

23. The method of claim 16 wherein said at least one additional personal care component comprises a monomeric surfactant selected from the group consisting of anionic surfactants, amphoteric surfactants, and combinations of two or more thereof.

24. The method of claim 10 wherein said low-DP polymerized surfactant is an SGA.

* * * * *